US010029025B2

(12) United States Patent
Nettesheim

(10) Patent No.: US 10,029,025 B2
(45) Date of Patent: Jul. 24, 2018

(54) SYSTEM AND METHOD FOR REDUCING GERMS BY MEANS OF PLASMA

(71) Applicant: Relyon Plasma GmbH, Regensburg (DE)

(72) Inventor: Stefan Nettesheim, Regensburg (DE)

(73) Assignee: Relyon Plasma Gmbh, Regensburg (DE)

( * ) Notice: Subject to any disclaimer, the term of this patent is extended or adjusted under 35 U.S.C. 154(b) by 246 days.

(21) Appl. No.: 14/996,886

(22) Filed: Jan. 15, 2016

(65) Prior Publication Data

US 2016/0129142 A1     May 12, 2016

Related U.S. Application Data

(63) Continuation of application No. PCT/IB2014/062922, filed on Jul. 7, 2014.

(30) Foreign Application Priority Data

Jul. 15, 2013    (DE) .................. 10 2013 107 448

(51) Int. Cl.
| | |
|---|---|
| *A61L 2/14* | (2006.01) |
| *A61L 9/22* | (2006.01) |
| *H01J 37/32* | (2006.01) |
| *H05H 1/24* | (2006.01) |

(52) U.S. Cl.
CPC ............... *A61L 2/14* (2013.01); *A61L 9/22* (2013.01); *H01J 37/32807* (2013.01); *H01J 37/32816* (2013.01); *H05H 1/2475* (2013.01); *A61L 2202/11* (2013.01); *A61L 2202/25* (2013.01); *A61L 2209/132* (2013.01); *H05H 2001/2481* (2013.01)

(58) Field of Classification Search
CPC ........................................................ A61L 2/14
See application file for complete search history.

(56) References Cited

U.S. PATENT DOCUMENTS

| | | | |
|---|---|---|---|
| 3,881,503 A * | 5/1975 | Fox ........................... | A61L 2/18 |
| | | | 134/103.1 |
| 8,994,271 B2 | 3/2015 | Kindel et al. | |
| 2008/0179286 A1* | 7/2008 | Murokh ..................... | A61L 2/14 |
| | | | 216/67 |
| 2008/0260578 A1 | 10/2008 | Engemann et al. | |
| 2009/0009090 A1* | 1/2009 | Viol ..................... | H05H 1/2406 |
| | | | 315/111.21 |
| 2011/0095688 A1* | 4/2011 | Bisges ..................... | A61L 2/14 |
| | | | 315/111.21 |

(Continued)

FOREIGN PATENT DOCUMENTS

| | | |
|---|---|---|
| CN | 101259036 A | 9/2008 |
| DE | 10 2004 049 783 B4 | 4/2006 |

(Continued)

*Primary Examiner* — Donald R Spamer
(74) *Attorney, Agent, or Firm* — Simpson & Simpson, PLLC

(57) ABSTRACT

Disclosed is a system for reducing germs by means of plasma. To this end, a piezoelectric transformer is associated with a dielectric film. The peripheral edge of the dielectric film encloses an area to be sterilized, a cavity being formed thereby. A high-voltage end of the piezoelectric transformer is facing a side of the dielectric film facing away from the cavity. The plasma is ignited within the cavity.

19 Claims, 7 Drawing Sheets

(56) References Cited

U.S. PATENT DOCUMENTS

2012/0046602 A1* 2/2012 Morfill .............. A61L 2/0011
604/23
2012/0271225 A1 10/2012 Stieber et al.

FOREIGN PATENT DOCUMENTS

| | | |
|---|---|---|
| DE | 20 2008 008 980 | 10/2008 |
| DE | 10 2007 054 161 A1 | 5/2009 |
| DE | 10 2008 018 827 A1 | 10/2009 |
| DE | 20 2008 008 733 U1 | 12/2009 |
| DE | 10 2009 028 190 A1 | 2/2011 |
| DE | 10 2010 003 284 A1 | 9/2011 |
| DE | 10 2011 001 416 A1 | 9/2012 |
| EP | 2170022 | 3/2010 |
| JP | 2006156276 A | 6/2015 |
| WO | 2010/022871 A1 | 3/2010 |
| WO | 2010/034451 A1 | 4/2010 |
| WO | 2011/023478 A1 | 3/2011 |
| WO | 2011/055113 A1 | 5/2011 |
| WO | 2011/110191 A1 | 9/2011 |
| WO | 2012/158443 A2 | 11/2012 |

* cited by examiner

SYSTEM AND METHOD FOR REDUCING GERMS BY MEANS OF PLASMA

CROSS REFERENCE TO RELATED APPLICATIONS

This Application is filed under 35 U.S.C. § 120 and § 365(c) as a continuation application of International Application PCT/IB2014/062922, filed on Jul. 7, 2014, which application claims priority to German Patent Application 10 2013 107 448.0, filed on Jul. 15, 2013, which applications are incorporated herein by reference in their entirety.

FIELD OF THE INVENTION

The present invention relates to a system for germ reduction by means of plasma. Additionally the invention relates to method for reducing germs by means of plasma.

BACKGROUND OF THE INVENTION

The German patent DE 10 2008 018 827 B4 discloses an apparatus for generating a plasma by a piezo element. The piezo element has a primary and a secondary portion. The primary portion of the piezo element is driven by low voltage and high frequency. As a result a plasma is ignited by the high field on the surface of the secondary portion of the piezo element.

The German patent application DE 10 2007 054 161 A1 discloses a method for sterilization of elongated bodies. With the plasma treatment method described, a surface decontamination is achieved in order to kill micro-organisms and viruses by a low-temperature plasma. The method is characterized by various suitable additives added to the plasma in order to achieve an efficient killing of the micro-organisms or viruses. The method is applied to inorganic bodies.

The Chinese patent application CN 101259036 A discloses a micro plasma pen for removing freckles. The pen comprises a plasma-head for cleaning the skin, a housing with handle, a micro converter arranged in the housing with handle, a power control and a power module. The pen can output a high and variable plasma power, to which end an integrated circuit or a semiconductor microprocessor chip are mounted in the housing with handle, the circuit driving a piezoelectric transformer.

The international patent application WO 2010/034451 A1 discloses a plasma applicator for applying anon-thermal plasma to a surface. The device is in particular used for the plasma treatment of living tissue, and especially for the plasma treatment of wounds.

The German patent application DE 10 2009 028 190 A1 discloses an apparatus for generating a non-thermal atmospheric plasma. A HF-generator, a HF resonance coil with a closed ferrite core suitable for high frequency, an insulating body acting as gas nozzle as well as a high-voltage electrode mounted in the insulating body are arranged in a metal housing, acting as ground electrode, in such a way that the process gas is flowing around or through them, respectively.

The German patent application DE 10 2011 001 416 A1 discloses a plasma treatment apparatus for the treatment of wounds or afflicted portions of skin. The plasma treatment apparatus has two flexible planar electrodes for generating a non-thermal plasma. The two planar electrodes each comprise at least one electric conductor, wherein the conductors are interwoven with each other. To the outer side of the planar electrodes, facing the surface to be treated, a wound contact layer of antiseptically treated material is detachably fixed.

The international patent application WO 2010/022871 A1 discloses an apparatus for treating wounds with a non-thermal plasma. The plasma includes a partially ionized carrier gas and at least one additive, which preferentially has a sterilizing effect, improving the healing of the wounds.

The international patent application WO 2010/034451 A1 discloses a plasma applicator for applying a non-thermal plasma to a surface, in particular for the plasma treatment of living tissue, and especially for the plasma treatment of wounds. The plasma applicator includes a cover lid for covering a part of the surface. In this way a cavity is created between the cover lid and the surface. The non-thermal plasma is provided in the cavity, and in addition the cavity can be flushed with gas. Likewise, a pump is provided for removing gas from the cavity.

The international patent application WO 2011/023478 A1 discloses an apparatus for the planar treatment of portions of human or animal skin with a cold plasma under atmospheric pressure. Thereunto, a dielectrically hindered discharge is provided, which affects the surface. The apparatus comprises at least a flexible insulating material, a flexible high-voltage electrode, a flexible dielectric, a flexible grounded electrode and a gas supply. The flexible high-voltage electrode is embedded in the insulating elastomer.

The international patent application WO 2011/110191 A1 discloses an apparatus for the treatment of a planar object with a low-temperature plasma, in particular for sterilizing the object. The low-temperature plasma is applied on a surface of the object, wherein the low-temperature plasma is applied through an envelope, so that the low-temperature plasma treatment permeates through the cover.

The international patent application WO 2012/158443 A2 discloses an apparatus for generating a cold plasma. The apparatus includes a hand-held nozzle by which the plasma is directed onto the location to be treated for healing wounds, improving anomalies of the skin surface, and for killing germs.

The German utility model DE 20 2008 008 733 U1 discloses an apparatus for the treatment of objects. The objects to be treated are placed into a container. At least one inner electrode at the inside of the container and an outer electrode cooperating with the at least one inner electrode are provided. The outer electrode is connected to a voltage source. A dielectric is provided between the outer electrode and the inner electrode. The electric discharge occurs at the inner electrode, so that a plasma forms.

The German patent DE 10 2004 049 783 B4 discloses an apparatus for processing goods with the help of an electric discharge. Here, too, a reception chamber is formed, into which the object to be treated is placed. At the outside of the chamber at least two electrodes are provided, which are capacitively coupled to an inner electrode. The plasma is generated in the chamber.

The German patent application DE 10 2010 003 284 A1 discloses a method for the chemical activation of process gases in closed volumes. The dielectrically hindered discharge is generated within the volume. The field-generating electrodes therein are in close outer surface contact with the dielectric material limiting the volume.

The international patent application WO 2011/055113 A1 describes the generation of a plasma and the use of the plasma generation apparatus. The apparatus for generating the plasma uses a first electrode and a second electrode. The second electrode has a plurality of slits, and thus forms a uniform topology of the generated plasma.

BRIEF SUMMARY OF THE INVENTION

It is an object of the invention to provide a system for germ reduction by means of plasma, which is cost efficient, easy to use without any big effort in terms of apparatus and safety. In addition, a planar and homogeneous treatment of an area shall be achieved.

The above object is achieved by a system for reducing germs by means of plasma including a housing, a piezoelectric transformer arranged in said housing, an opening form in said housing, wherein a high-voltage end of said piezoelectric transformer points to said opening, a dielectric film with a peripheral edge forms a cavity, wherein said dielectric film enclosing or surrounding an area to be sterilized, and said high-voltage end of said piezoelectric transformer is facing toward a side of the dielectric film which faces away from said cavity, and the plasma is ignitable within said cavity.

A further object of the invention is to provide a method for germ reduction by means of plasma, which is cost efficient, easy to use without any big effort in terms of apparatus and safety. In addition, a planar and homogeneous treatment of an area shall be achieved.

The above object is achieved by a method for reducing germs by means of plasma, the method includes the steps of applying a dielectric film no that said dielectric film encloses or surrounds an area to be sterilized and forms a cavity, facing a said high-voltage end of a piezoelectric transformer toward a side of the dielectric film which faces away from said cavity, and igniting the plasma within said cavity.

The advantage of the system according to the invention is that a planar and homogeneous treatment of a surface or an area to be sterilized is possible. The film can be adapted to the prevalent conditions, so that the system according to the invention is suitable for a variety of uses. In addition, the plasma generation does not require an excitation voltage of several kilovolts.

According to the system according to the invention the plasma can be ignited without active counter electrode in the cavity, wherein the plasma is excited only by capacitive field transmission in the cavity.

In an embodiment, the dielectric film may be reinforced by an electrically conductive layer in a planar area. The electrically conductive layer distributes the electric field in the plane defined by the electrically conductive layer, no that damage by a local electric breakdown is avoided. The conductive layer therein is applied on a part of the side of the dielectric film facing the piezoelectric transformer or facing away from the piezoelectric transformer.

The piezoelectric transformer therein is associated to the dielectric film or the conductive layer of the dielectric film in such a way that the high-voltage end of the piezoelectric transformer is in mechanical and form-locked contact with the dielectric film or the conductive layer.

Furthermore the high-voltage end of the piezoelectric transformer may be firmly attached to a planar electrode, which is composed of dielectric and electrically conductive material.

The piezoelectric transformer may be arranged in handheld device along with a printed circuit board and a control circuit for exciting the piezoelectric transformer. The handheld device has a housing, wherein the high-voltage end of the piezoelectric transformer points to an opening in the housing.

Within the housing a first pressure is provided, wherein the first pressure is smaller than the ambient pressure. This condition ensures that the dielectric film is and remains sucked to the opening of the housing. In this way it is guaranteed that the high-voltage end of the piezoelectric transformer is in form-locked contact with the dielectric film during the entire application of the low-temperature plasma. For generating the first pressure within the housing, the housing may be provided with a fan wheel removing air from the interior of the housing and thus generating the required reduced pressure.

The cavity enclosing or surrounding the area to be sterilized is formed by the peripheral edge of the dielectric film being glued to the body exhibiting the area to be sterilized. A further possibility is that the cavity is at least partially filled with a porous or fibrous material supporting a homogeneous gas discharge in the cavity.

According to a further embodiment of the invention the cavity may be formed by a dielectric film completely surrounding the object to be sterilized. The cavity may also be filled with a process gas.

For supplying energy to the piezoelectric transformer an accumulator or a connection for a standard mains adapter may be provided. The system according to the invention is used for reducing or killing germs in the context of the human or animal body. To this end the area to be sterilized is located within a cavity which is formed by a dielectric film being connected with the human or animal body.

Likewise the system according to the invention is used for reducing or killing germs in food or other objects to be hygienically packed. Herein the dielectric film completely surrounds the food or the objects to be hygienically packed.

According to the invention, alternating electric fields of high local field strength are generated by the piezoelectric transformer, wherein also a gas discharge can be ignited in a cavity limited by a thin dielectric film. This gas discharge is most efficient if the high-voltage side of the piezoelectric transformer is brought into form-locked contact (i.e., without gap) with the dielectric film. For easier and safe handling the piezoelectric transformer may be arranged in a hand-held device, wherein the hand-held device may be designed for battery based or accumulator based operation. It is also possible for the hand-held device to be connected to a mains supply. Furthermore, it has turned out to be advantageous if a porous structure is provided in the cavity. The gas discharge ignites particularly homogeneously in a porous structure, as in small pores the mean free path in the gas phase at atmospheric pressure is comparable with the pore size (1 to 10 μm) of the porous structure.

The inventive method can be applied to human beings or animals in order to reduce germs in an area (wound) of said human or animal body to be sterilized. Here the cavity is formed by gluing said peripheral edge of said dielectric film to the area of the human or animal body to be sterilized. The cavity encloses said area of the human or animal body.

A further embodiment of the inventive method is that the dielectric has a peripheral edge, and said cavity is formed by gluing said peripheral edge of at least one dielectric film together to form said cavity. The cavity surrounds food or other goods to be packed hygienically for a reduction of germs or killing of germs.

Further advantages and advantageous embodiments of the invention are the subject of the following figures and their description.

There is shown in:

DETAILED DESCRIPTION OF THE INVENTION

Identical reference signs are used for like elements of the invention or elements of like function. The embodiments shown only are a possibility of how the system for germ reduction by means of a plasma may be configured.

Figure 1:
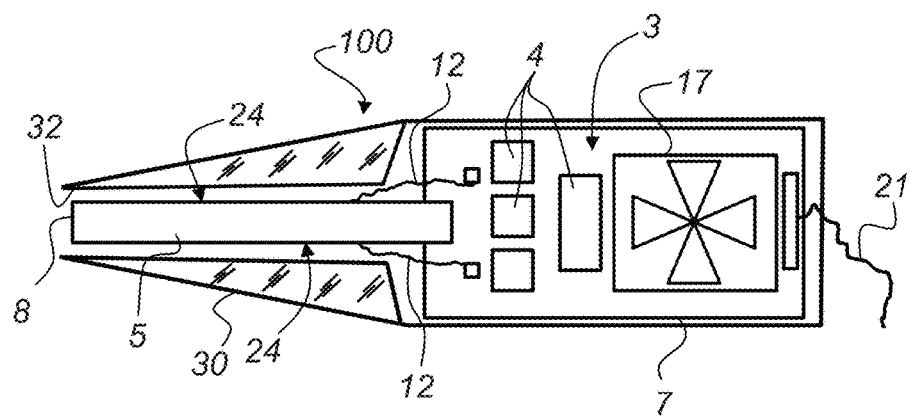
FIG. 1 is a schematic view of the principle configuration of the hand-held device, which in the present invention is used for generating a plasma at atmospheric pressure.

A schematic top view of a hand-held device 100 used with the present invention is shown in FIG. 1. The piezoelectric transformer 5 is arranged in a housing 30. For driving, the piezoelectric transformer 5 is connected with a printed circuit board 7. The printed circuit board 7, via a plurality of electronic elements 4, implements a control circuit 3. By means of the control circuit 3 it is possible to excite the piezoelectric transformer 5 at its resonance frequency. The control circuit 3 for the piezoelectric transformer 5 may be connected with an external energy supply, which is an ordinary standard mains adapter (not shown), connected with the housing 30 of the piezoelectric transformer 5 via a cable 21. Likewise the energy supply can be done with an accumulator. A combination of accumulator and standard mains supply is also conceivable. The driving voltage is applied to a respective side surface 24 of the piezoelectric transformer 5 by the control circuit 3 of the printed circuit board 7 via a respective electric connection 12. By the excitation voltage applied to the side surfaces 24 of the piezoelectric transformer 5 the required high voltage is generated at the high-voltage end 8 of the piezoelectric transformer 5. In or at the housing 30 furthermore a fan 17 is provided, generating a pressure in the housing 30 which is smaller than the ambient pressure. In this way it is possible that a dielectric film 6 is always in contact with the high-voltage end 8 of the piezoelectric transformer 5.

Figure 2:
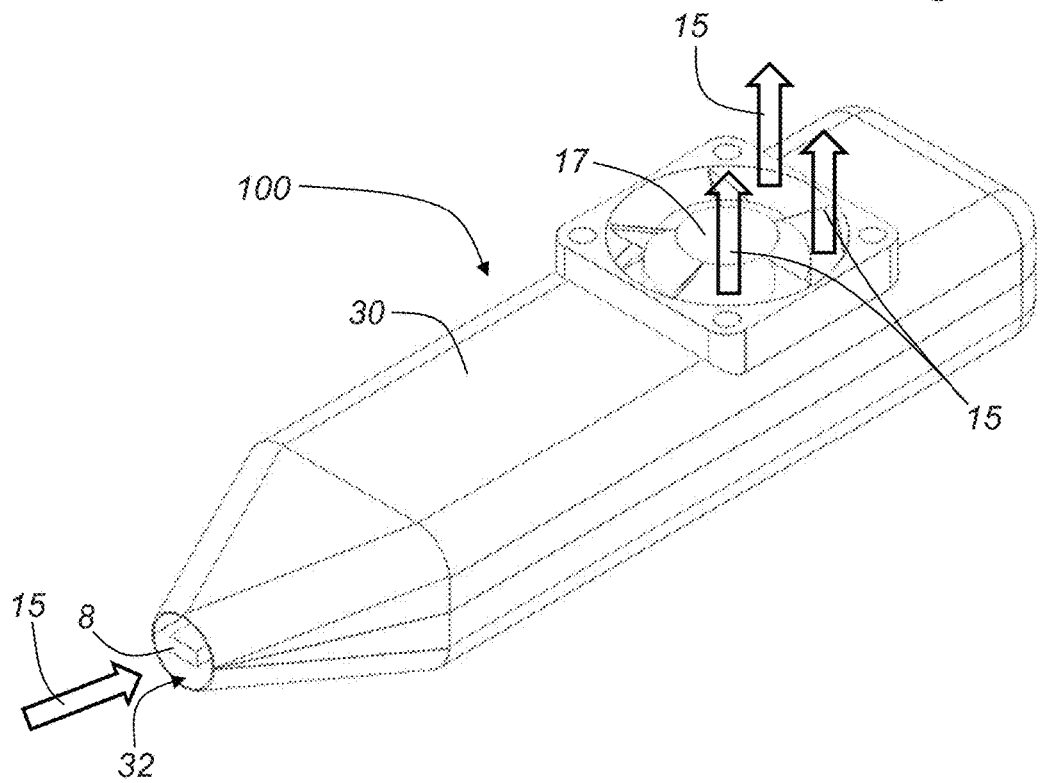
FIG. 2 is a perspective view of the hand-held device from the outside, wherein the piezoelectric transformer is arranged in a housing.

In FIG. 2, a perspective view of an embodiment of the housing 30 is shown. In the housing 30 the piezoelectric transformer 5 is arranged. The high-voltage end 8 of the piezoelectric transformer 5 is accessible via an opening 32 of the housing 30. The fan 17, connected with the housing, generates a flow of the ambient gas so that the pressure within the housing 30 is smaller than the ambient pressure. In this way it is achieved that the dielectric film 6 is sucked to the opening 32 of the housing 30. Thus it is also ensured that during the use of the hand-held device 100 the high-voltage end 8 of the piezoelectric transformer 5 is always in contact with the dielectric film 6.

Figure 3:
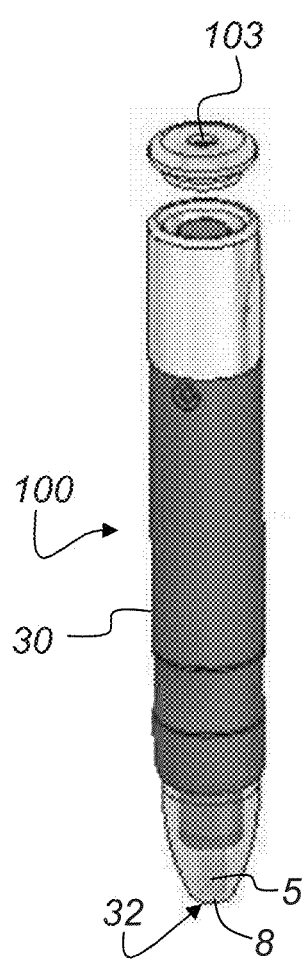
FIG. 3 is an embodiment of a hand-held device used in the system according to the invention.

FIG. 3 shows an embodiment of the hand-held device 100 which can be used for the reduction of germs of an area to be treated which is enclosed or surrounded by the dielectric film 6. The hand-held device 100 has a connection 103 for a cable of a standard mains adapter. The hand-held device 100 is of cylindrical shape, so that in the interior of the housing a fan (not shown here) may also be provided, which generates the flow 15 of ambient gas shown in FIG. 2. The flow 15 enters through the opening 32 of the housing 30, so that the dielectric film 8 is in contact with the opening 32 of the housing 30 and the high-voltage end 8 of the piezoelectric transformer 5.

Figure 4:
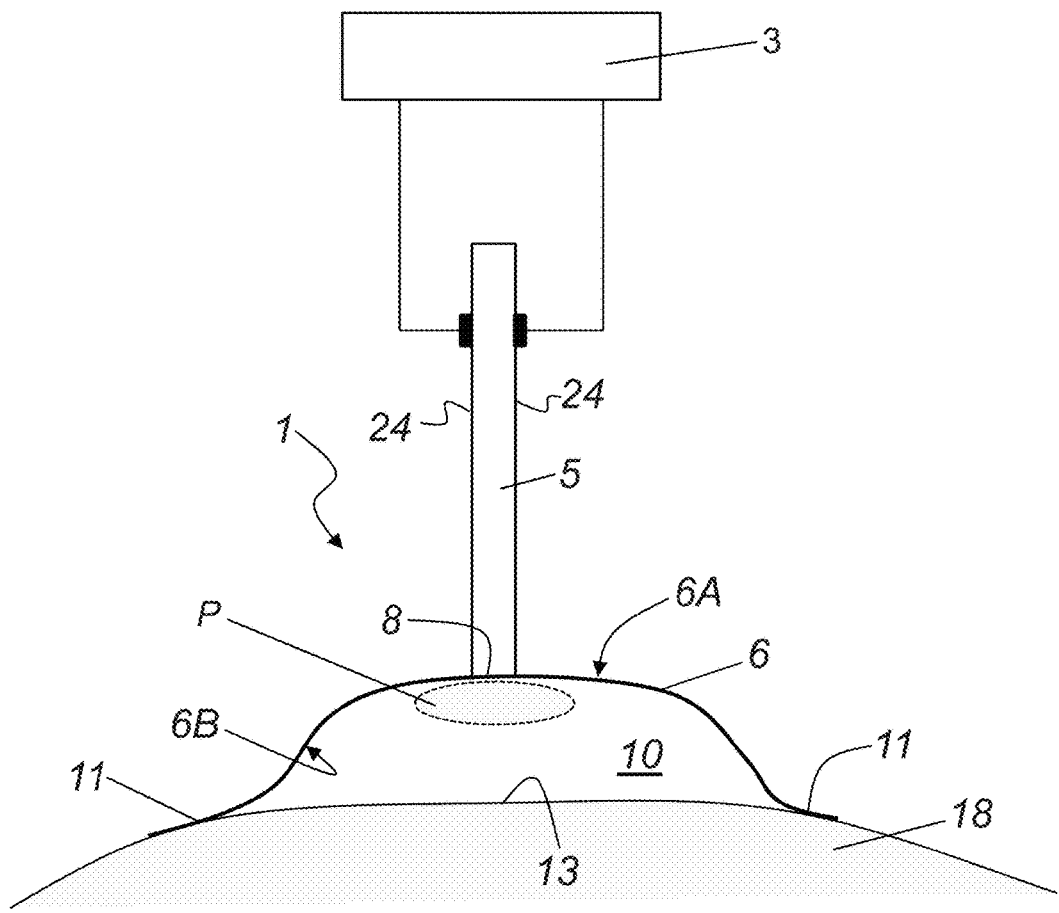
FIG. 4 is a schematic view of the association of the piezoelectric transformer with a dielectric film which forms the cavity.

In FIG. 4, a system 1 according to the invention is schematically shown. The high-voltage end 8 of the piezoelectric transformer 5 is in contact with a dielectric film 6. The dielectric film 6 has a peripheral edge 11, which is glued to a body 18 around an area 13 to be sterilized. The dielectric film 6 has a side 6A facing away from the area 13 to be sterilized, and a side 6B facing the area to be sterilized. The high-voltage end 8 of the piezoelectric transformer 5, during application, is in contact with the side 6A of the film 6 facing away from the area 13 to be sterilized. The piezoelectric transformer 5 is connected with a control circuit 3. To this end the control circuit 3 is electrically connected to two respectively opposite sides 24 of the piezoelectric transformer 5. By excitation 3 via the control circuit a plasma P (gas discharge) is generated, which forms within the cavity 10. Put differently, the plasma 10 is generated on the side 6B of the dielectric film 6 facing the area 13 to be sterilized.

Figure 5:
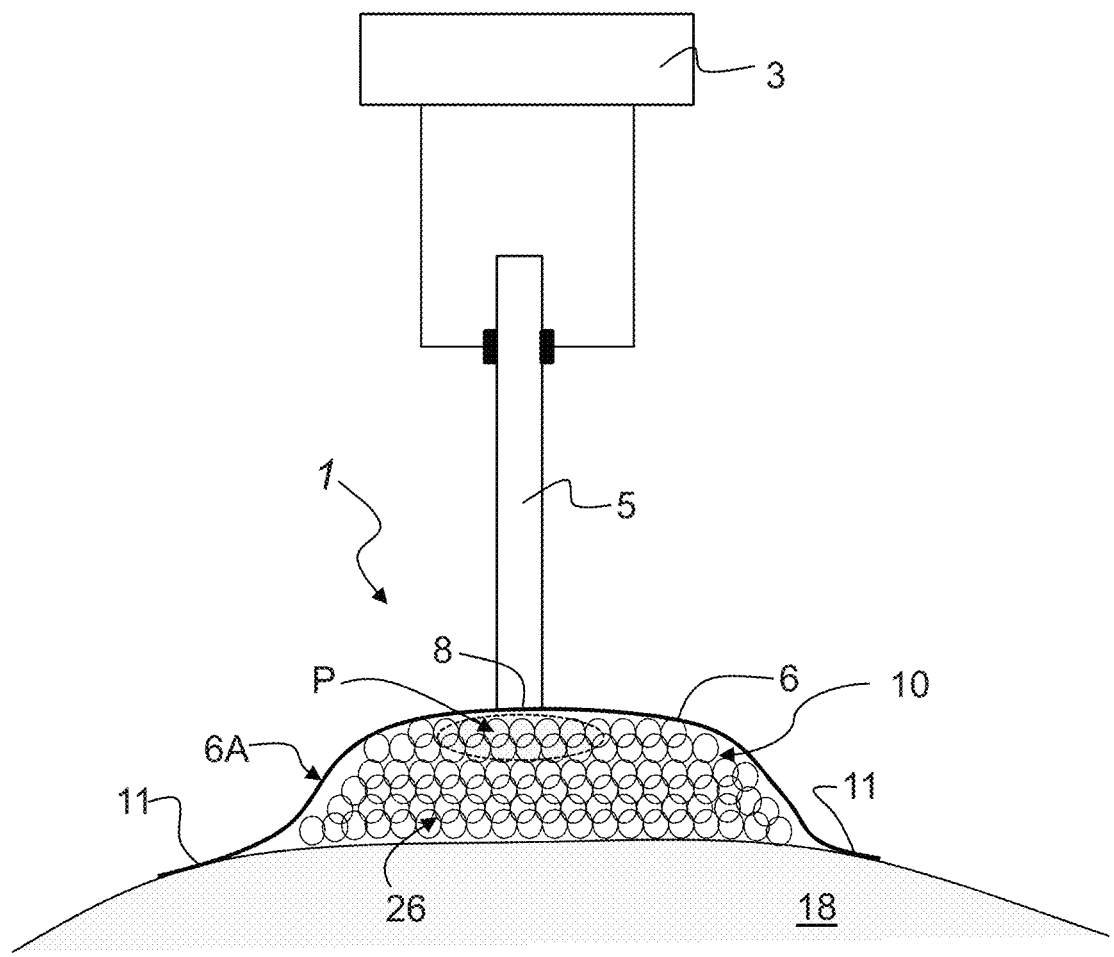
FIG. 5 is a schematic view of the association of the piezoelectric transformer with the dielectric film, wherein porous material is provided in the cavity.

FIG. 5 shows a further embodiment of system 1, wherein the high-voltage end 8 of the piezoelectric transformer 5 is also associated with the side 6A of the dielectric film 6 facing away from the area 13 to be sterilized. As already mentioned in the description of FIG. 4, the dielectric film 6 is glued with the peripheral edge 11 to the body 18, so that the cavity 10 forms around the area 13 to be sterilized. In the embodiment shown here, the cavity 10 is filled with a porous or fibrous material 26. The porous or fibrous material 26 may also be a distancing body which is placed on the area 13 to be sterilized and is then surrounded with the dielectric film 6 in such a way that the peripheral edge 11 of the dielectric film 6 is glued to the body 18. The porous or fibrous material 26 therein facilitates the generation of the plasma P (gas discharge) in the cavity 10. The porous or fibrous material 26 has the advantage that here the gas discharge ignites particularly homogeneously. The small pores in the fibrous or porous material 26 therein are formed such that the mean free path of the gas discharge in the gas phase at atmospheric pressure is comparable to the pore size (1 to 10 μm) of the material 26.

Figure 6:
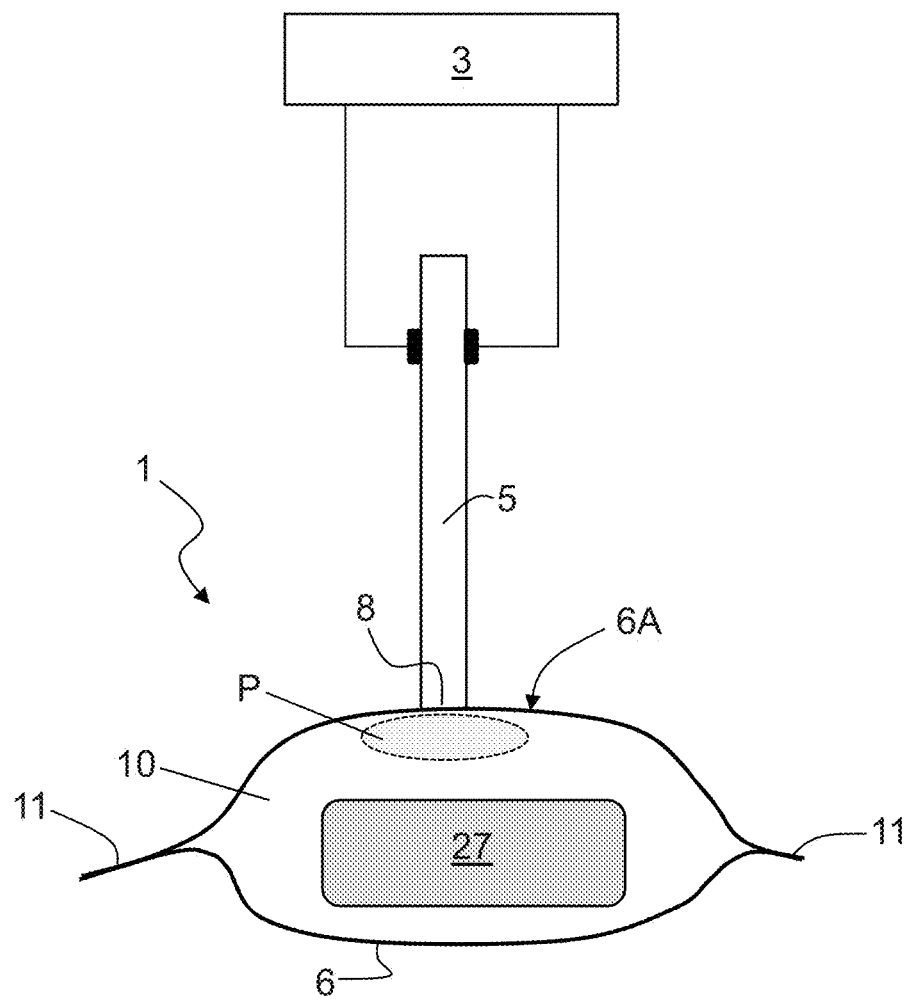
FIG. 6 is a schematic view of the association of the piezoelectric transformer with a cavity, wherein the dielectric film completely surrounds an object to be sterilized.

FIG. 6 shows a further embodiment of the system 1, wherein the object 27 to be sterilized is completely surrounded by the dielectric film 6. Here, too, the high-voltage end 8 of the piezoelectric transformer 5 faces the side 64 of the dielectric film 6 facing away from the cavity 10. Inside the cavity 10 the plasma P is ignited, in order to sterilize the object 27. The cavity 10 may for example be formed by two dielectric films 6 being glued to each other with their peripheral edges 11.

Figure 7:
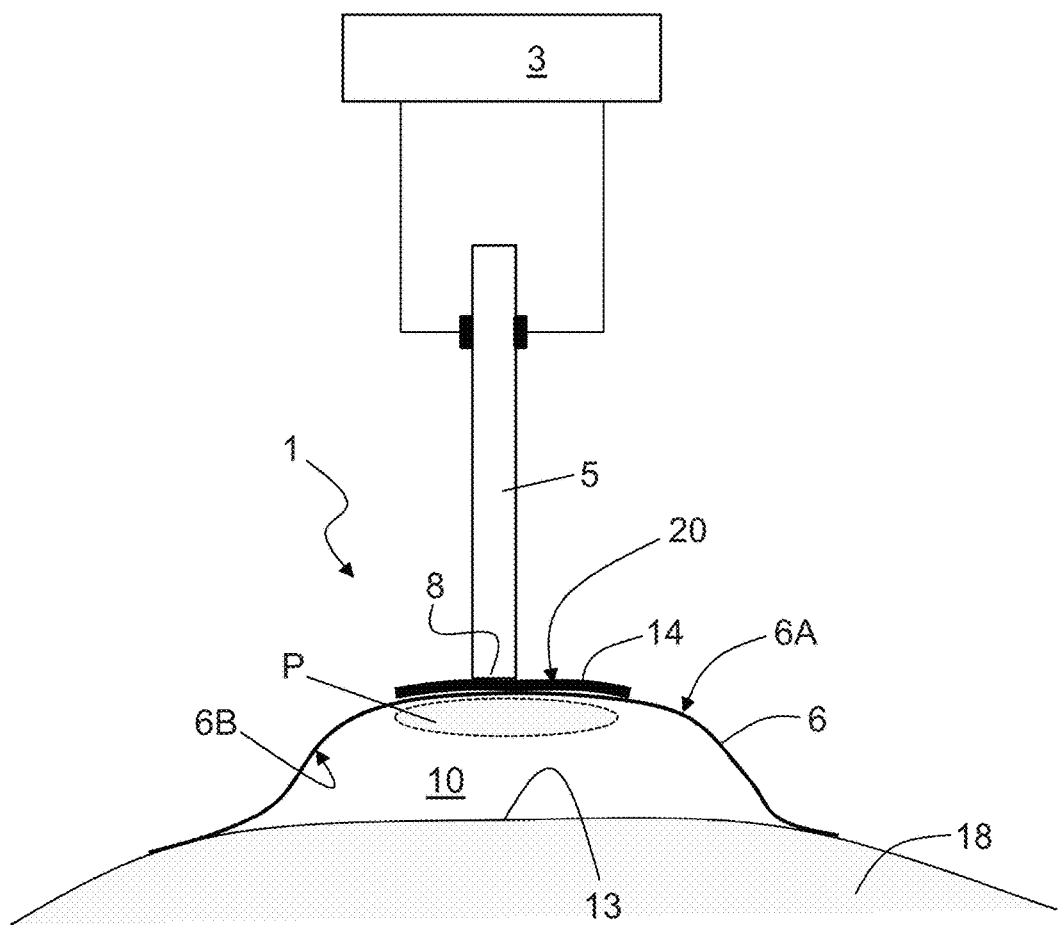
FIG. 7 is a schematic view of the piezoelectric transformer in connection with the dielectric film, wherein the dielectric film carries an electrically conductive layer; and, FIG. 8 is a schematic view of the piezoelectric transformer arranged in a housing and associated with the dielectric film for generating the plasma.

FIG. 7 shows a further embodiment of the system 1 according to the invention. In order to optimally distribute the field strength, a conductive layer 14 is applied on the dielectric film 6. The conductive layer 14 may be applied on the side 6A of the dielectric film 6 facing away from the cavity 10 or on the side 6B of the dielectric film 6 facing the cavity 10. Therein the high-voltage end 8 of the piezoelectric transformer 5 is in direct contact with the conductive layer 14, if this is on the side 6A of the dielectric film 6 facing away from the cavity 10. Instead of the conductive layer 14, the high-voltage end 8 of the piezoelectric transformer 5 may be provided with a planar electrode 20, which in turn is in contact with the side 6A of the dielectric film 6 facing away from the cavity 10. The area 13 to be sterilized, as has already been mentioned in the description of the preceding figures, is defined by the dielectric film 6, which is applied on a body 18 and glued to it.

Figure 8:
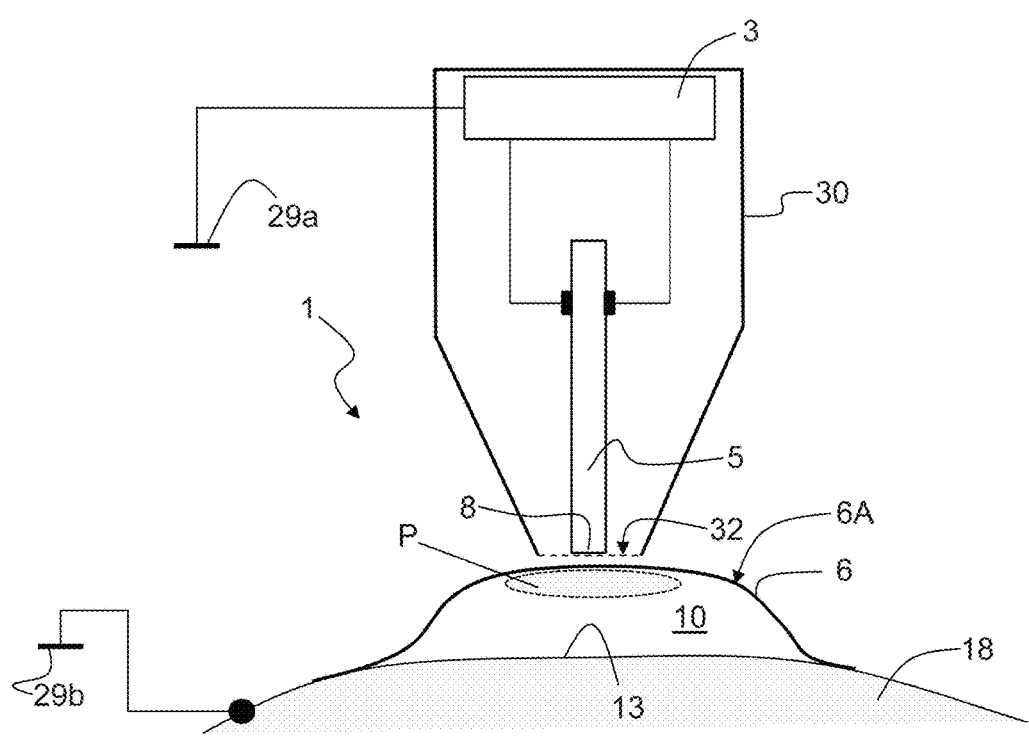

FIG. 8 shows an embodiment of the system 1 according to the invention, wherein the piezoelectric transformer 5 is arranged in a housing 30. The high-voltage end 8 of the piezoelectric transformer 5 is in contact with the side 6A of the dielectric film 6 facing away from the cavity 10, via the opening 32 of the housing 30. In order to achieve a gapless coupling of the high-voltage end 8 of the piezoelectric transformer 5, a reduced pressure is applied to the housing 30, so that the dielectric film 6 is sucked to the opening 32 of the housing 30. The generation of the plasma P (gas discharge) in the cavity 10 is facilitated by the control circuit 3 for the piezoelectric transformer 5 and the body 18, on which the area 13 to be sterilized is located, being connected with a common ground reference 29a and 29b.

It is obvious to a skilled person that the features of the system 1 according to the invention described in the various embodiments can be freely combined with each other, in order to achieve the optimal sterilization or killing of micro-organisms and viruses on the surface of the area 13 to be sterilized.

LIST OF REFERENCE NUMBERS 1 system
3 control circuit
4 electronic elements
5 piezoelectric transformer
6 dielectric film
6A side of film facing away from the cavity
6B side of film facing the cavity
7 printed circuit board
8 high-voltage end
10 cavity
11 peripheral edge
12 electric connection
13 area to be sterilized
14 conductive layer
15 flow of ambient gas
17 fan
18 body
20 planar electrode
21 cable of mains adapter
24 side of piezoelectric transformer
26 porous or fibrous material
29a ground reference
29b ground reference
30 housing
32 opening
100 hand-held device
101 accumulator
103 connection

What is claimed is:

1. A system for reducing germs by means of plasma comprising:
   a housing;
   a piezoelectric transformer arranged in said housing;
   an opening form in said housing, wherein a high-voltage end of said piezoelectric transformer points to said opening form;
   a dielectric film with a peripheral edge forms a cavity, wherein said dielectric film encloses or surrounds an area to be sterilized;
   said high-voltage end of said piezoelectric transformer is facing toward a side of the dielectric film which faces away from said cavity, and a plasma is ignitable within said cavity; and,
   a first pressure exists within said housing and a second pressure exists in an environment, wherein said second pressure being higher than said first pressure and the dielectric film is sucked to said opening, and said high-voltage end of said piezoelectric transformer is in form-locked contact with said dielectric film.

2. The system of claim 1, wherein a conductive layer is applied on a portion of said side of said dielectric film facing said piezoelectric transformer.

3. The system of claim 2, wherein said high-voltage end of said piezoelectric transformer is in mechanical and form-locked contact with said conductive layer.

4. The system of claim 1, wherein a conductive layer is applied on a portion of a second side of said dielectric film facing away from said piezoelectric transformer.

5. The system of claim 4, wherein said high-voltage end of said piezoelectric transformer is in mechanical and form-locked contact with said dielectric film.

6. The system of claim 1, wherein said high-voltage end of said piezoelectric transformer is firmly connected with a planar electrode which is composed of dielectric and electrically conductive material.

7. The system of claim 1, wherein said piezoelectric transformer and a printed circuit board with a control circuit for exciting said piezoelectric transformer are arranged within said housing and thus form a hand-held device.

8. The system of claim 1, wherein a fan wheel is provided within said housing for generating said required first pressure within the housing.

9. The system of claim 1, wherein said cavity is formed by said peripheral edge of said dielectric film being glued to an area of a body to be sterilized.

10. The system of claim 9, wherein said cavity is at least partially filled with a porous or fibrous matter supporting a homogeneous gas discharge.

11. The system of claim 9, wherein said cavity is filled with a process gas.

12. The system of claim 1, wherein said cavity is formed by said dielectric film, which fully surrounds an object to be sterilized.

13. The system of claim 12, wherein said cavity is filled with a process gas.

14. The system of claim 1, wherein an energy supply of said piezoelectric transformer is at least one of an accumulator and a connection for a standard power supply.

15. A method for reducing germs by means of plasma comprising the steps of:
   applying a dielectric film so that said dielectric film encloses or surrounds an area to be sterilized and forms a cavity;

facing a high-voltage end of a piezoelectric transformer toward a side of the dielectric film which faces away from said cavity;

generating a first pressure within a housing for said piezoelectric transformer, wherein said high-voltage end of said piezoelectric transformer points to an opening of the housing and wherein said first pressure being smaller than a second pressure in an environment and the dielectric film is sucked to said opening, so that said high-voltage end of said piezoelectric transformer is in form-locked contact with said dielectric film; and, igniting a plasma within said cavity.

16. The method of claim 15, wherein said dielectric film has a peripheral edge and said cavity is formed by said peripheral edge of said dielectric film being glued to an area of a human or animal body so that said cavity encloses said area of said human or animal body to be sterilized.

17. The method of claim 16, wherein said cavity is at least partially filled with a porous or fibrous matter supporting a homogeneous gas discharge.

18. The method of claim 15, wherein said dielectric film has a peripheral edge and said cavity is formed by gluing said peripheral edge of at least one of said dielectric film together to form said cavity, wherein said cavity surrounds food or other goods to be packed hygienically for a reduction of germs or killing of germs.

19. The method of claim 15, wherein said cavity is filled with a process gas.

* * * * *